(12) United States Patent
Heijnsdijk et al.

(10) Patent No.: US 6,400,648 B1
(45) Date of Patent: Jun. 4, 2002

(54) ULTRASONIC WAVEGUIDE

(75) Inventors: Alexander Marnix Heijnsdijk, Papendrecht; Jeroen Martin van Klooster, Tiel, both of (NL)

(73) Assignee: Krohne A.G. (CH)

( * ) Notice: Subject to any disclaimer, the term of this patent is extended or adjusted under 35 U.S.C. 154(b) by 26 days.

(21) Appl. No.: 09/706,104

(22) Filed: Nov. 3, 2000

(51) Int. Cl.[7] ................................................. G01F 1/66
(52) U.S. Cl. ...................................................... 367/152
(58) Field of Search ............................. 367/152; 73/644

(56) References Cited

U.S. PATENT DOCUMENTS 4,392,380 A * 7/1983 Caines ........................ 73/644

FOREIGN PATENT DOCUMENTS

| EP | WO96/41157 | | 12/1996 |
| JP | 2001-147143 A | * | 5/2001 |

* cited by examiner

*Primary Examiner*—Daniel T. Pihulic
(74) *Attorney, Agent, or Firm*—Cesari and McKenna, LLP

(57) ABSTRACT

An ultrasonic waveguide for guiding an ultrasonic signal situated in a predetermined frequency range is illustrated and described. The ultrasonic waveguide according to the invention is characterized in that it has a coiled foil whose layer thickness is considerably less than the smallest wavelength of the ultrasonic signal in the predetermined frequency range in the foil material. The result is that ultrasonic signal interference and attenuation in the ultrasonic waveguide due to scattering and dispersion are largely avoided.

11 Claims, 1 Drawing Sheet

ULTRASONIC WAVEGUIDE

Figure 1:
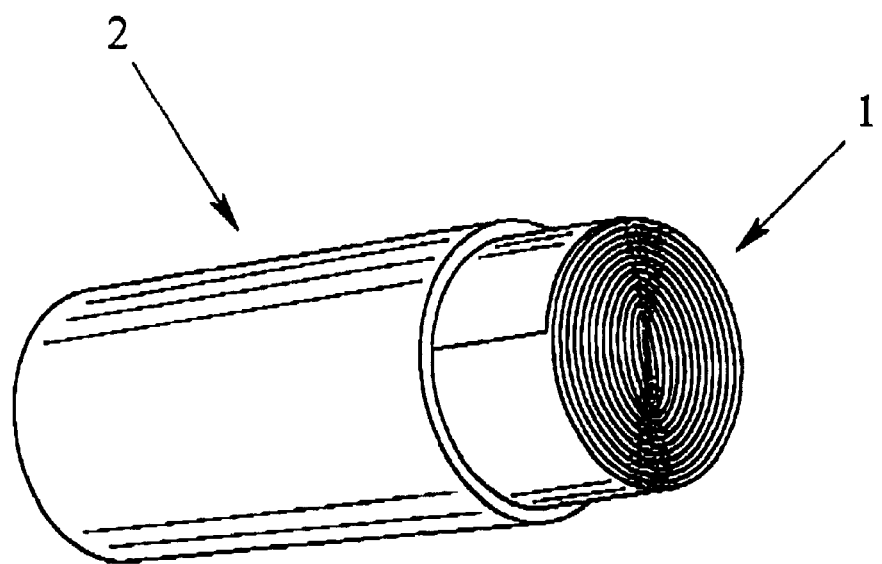

The invention relates to an ultrasonic waveguide for guiding an ultrasonic signal situated in a predetermined frequency range. Such ultrasonic waveguides are used in ultrasonic flowmeters, for example. A piezoelectric crystal with which ultrasonic signals are generated and/or ultrasonic signals are detected is typically used for an ultrasonic transducer in these ultrasonic flowmeters.

Piezoelectric crystals can no longer be used above a certain temperature, the so-called Curie point ($T_c$), because above $T_c$ there is no ferroelectric or ferromagnetic phase of the crystal, which is a requirement for its piezoelectric quality. If the flowing medium whose flow is to be measured with the ultrasonic flowmeter is very hot such that its temperature is above the Curie point of the piezoelectric crystal, a certain thermal insulation of the ultrasonic transducer from the hot medium is required for reliable operation of the ultrasonic flowmeter. Ultrasonic waveguides intended to ensure the best possible thermal insulation of the ultrasonic transducer from the hot medium, on the one hand, and transfer of the ultrasonic signal as free of loss and undistorted as possible, on the other hand, are used for such a thermal insulation. With such an ultrasonic waveguide, the ultrasonic signal generated by an ultrasonic transducer can then be input into the flowing medium while the actual ultrasonic transducer is spatially at a distance and thermally insulated from the hot medium.

Constructions such as those described in WO 96/41157, for example, are used as ultrasonic waveguides in conventional ultrasonic flowmeters. In this connection, a number of very thin, parallel rods are used as ultrasonic waveguides, and the individual rod diameters are each considerably smaller than the wavelength of the ultrasonic signal to be guided. For this, the rods are typically fitted closely together into a tube that provides the rods with lateral support and thus produces a compact ultrasonic waveguide. This conventional construction is problematic, however, in that rod diameters of significantly less than 0.1 mm are required for guiding ultrasonic signals with very high frequencies of more than 1 MHz. However, the production of such thin rods is quite complicated, demanding, and costly.

The technical problem of the invention is thus to provide an ultrasonic waveguide that is easy to manufacture, inexpensive, and with which high-frequency ultrasonic signals with frequencies of up to 20 MHz can be transferred with little attenuation and little interference.

According to the invention, the technical problem described above is solved by an ultrasonic waveguide that is characterized in that the ultrasonic waveguide has a coiled foil with a layer thickness considerably less than the smallest wavelength of the ultrasonic signal in the predetermined frequency range in the foil material. The invention thus makes use of the fact that ultrasonic signal attenuation and interference in an ultrasonic waveguide are dependent upon its dimensions. Ultrasonic signal attenuation and interference in the ultrasonic waveguide are essentially attributable to scattering and dispersion of the ultrasonic signal. These effects clearly recede, however, when the dimensions, i.e., the width and height of the ultrasonic waveguide are considerably less than the wavelength of the ultrasonic signal in the material of the ultrasonic waveguide. No scattering or dispersion of the ultrasonic signal can be expected if the ultrasonic waveguide extends practically infinitely.

With a foil that can be considered virtually infinitely extended in its plane of propagation, the decisive dimension is accordingly the foil's layer thickness, which therefore must be chosen suitably thin. If such a foil is coiled up, a rod-shaped ultrasonic waveguide meeting the requirements of practically scatter-free and dispersion-free ultrasonic guiding is obtained. Although with a coiled foil, adjacent foil layers lie directly on top of each other, the ultrasonic guiding characteristics of such a coiled foil do not correspond to those of a corresponding rod of a full material. Due to the boundary surfaces between the individual layers, each layer of the foil can be taken into consideration individually for the ultrasonic guiding characteristics of such a coiled foil; between the layers lying on top of each other, an impedance rise takes place that "insulates" from each other the individual layers for the ultrasonic guiding with respect to the guiding of the ultrasonic signal. In this respect, for a nearly scatter-free and dispersion-free guiding of the ultrasonic signal in the ultrasonic waveguide it is sufficient if each layer, by itself, meets the above-indicated geometric requirements, that is, essentially if its layer thickness is considerably less than the wavelength of the ultrasonic signal to be transferred in the material of the ultrasonic waveguide.

When sizing the ultrasonic waveguide according to the invention with a coiled foil, it should, therefore, first be verified what maximum frequency an ultrasonic signal to be guided through the ultrasonic waveguide has, such that the layer thickness of the foil to be used can be selected accordingly thin whereby scattering and dispersion of the ultrasonic signal in the ultrasonic waveguide can be largely suppressed.

The ultrasonic waveguide according to the invention can be used in all wavelength ranges from the range of audibility up to frequencies above 20 MHz. It is preferable, however, to use the ultrasonic waveguide according to the invention in a frequency range of 15 kHz to 20 MHz, with the foil layer thickness then being less than 0.1 mm.

A number of materials can be used for the coiled foil of the ultrasonic waveguide according to the invention, but the foil is preferably made of metal and/or ceramic and/or plastic.

An ultrasonic waveguide with the aforementioned good guiding qualities can already be obtained with a coiled foil by itself. It is preferably provided for, however, to insert the foil—preferably with a snug fit—into a tube. In the process, the tube stabilizes the ultrasonic waveguide and facilitates its installation into an ultrasonic flowmeter device, for example. A number of materials can, in turn, be used for the tube itself, but the tube is preferably made of metal.

An ultrasonic transducer is typically provided for at one end of the coiled foil, in such a way that ultrasonic signals can be input into the ultrasonic waveguide and ultrasonic signals can be received from the ultrasonic waveguide. The ultrasonic transducer, which generally has a piezoelectric crystal, can be mounted directly on an unfinished end surface of the foil layers for this purpose. It is preferably provided for, however, to weld the ends of the ultrasonic waveguide having the coiled foil. Welding with a TIG process (tungsten inert gas) is particularly preferred. A particularly smooth surface and thus an optimal capacity for feeding the ultrasonic signal into the ultrasonic waveguide according to the invention is achieved when the welded ends are faced after welding.

According to a preferred further development of the invention, it is provided for that the foil's layer thickness changes from the inside toward the outside. The ultrasonic waveguide can also be provided with several coiled foils with different layers and/or different materials, however. With these measures, it is achieved that the ultrasonic signal emitted by the ultrasonic waveguide can be shaped in a predetermined manner and thus guided and/or focused according to specific applications, for example. This possibility is based on the fact that the propagation rate of the ultrasonic signal in the ultrasonic waveguide depends on the respective impedance and thus, among other things, on the layer thickness of the respective foil layer in which the corresponding portion of the ultrasonic signal is guided. The same applies to the various propagation rates of the ultrasonic signal in different materials.

The ultrasonic waveguide according to the invention is quite versatile. It is preferably installed in an ultrasonic flowmeter intended to determine the flow of a high temperature medium, however.

In detail, there are numerous possibilities for designing and further developing the ultrasonic waveguide according to the invention. For this, the dependent patent claims, on the one hand and, on the other hand, the following detailed description of a preferred embodiment of the invention in connection with the drawings are referred to.

Figure 2:
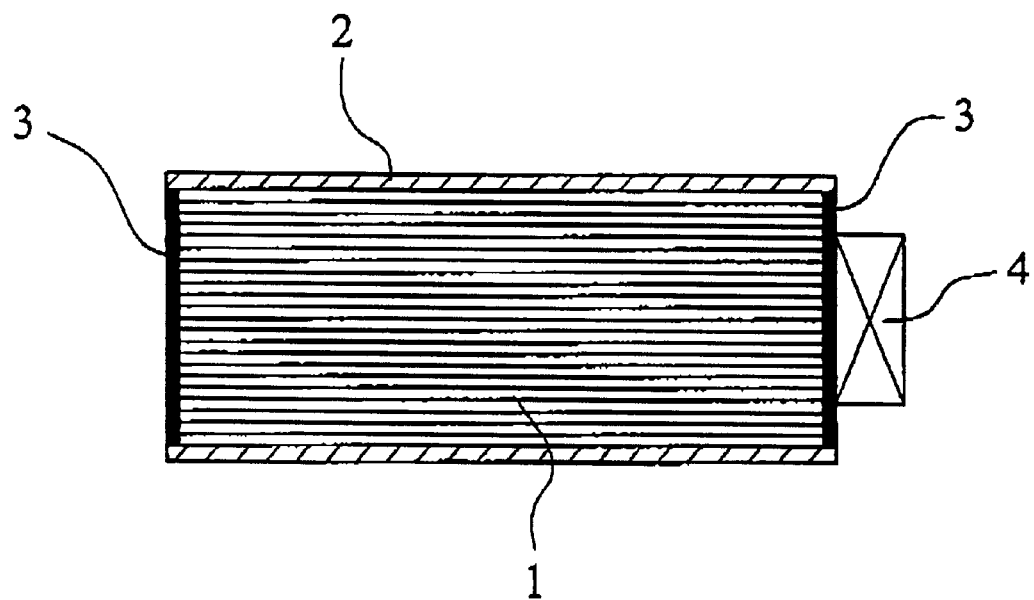

In the drawings:

FIG. 1 in schematic form, an ultrasonic waveguide according to a preferred embodiment of the invention, and FIG. 2 in schematic form, an ultrasonic waveguide according to a preferred embodiment of the invention with connected ultrasonic transducer.

FIG. 1 shows in schematic form an ultrasonic waveguide according to a preferred embodiment of the invention, that has a coiled foil 1 that is inserted into a tube 2 with a snug fit. According to the preferred embodiment of the invention illustrated in FIG. 1, the foil 1 as well as the tube 2 are made of special steel. The illustration of the ultrasonic waveguide in FIG. 1 is not true to scale. The foil's 1 layer thickness is namely 0.1 mm in the present case, such that even ultrasonic signals with a frequency well above 1 MHz can still be guided without serious scattering and dispersion effects. The length of the ultrasonic waveguide according to the first preferred embodiment of the invention is 0.6 m, and the tube 2 has a wall thickness of 1 mm and an inner diameter of 14 mm. With this ultrasonic waveguide, attenuation of less than 5 dB/m can be achieved for an ultrasonic signal with a frequency of 1 MHz.

FIG. 2 shows an ultrasonic waveguide according to a preferred embodiment of the invention with welded and faced ends 3 and an ultrasonic transducer 4 connected to one of these ends 3. An extremely smooth surface is obtained by means of TIG welding and subsequent facing of the ends of the ultrasonic waveguide, thus making possible an optimal transfer in the ultrasonic waveguide of the ultrasonic signals generated in the ultrasonic transducer 4 and, respectively, an interference-free reception of ultrasonic signals from the ultrasonic waveguide by the ultrasonic transducer 4.

What is claimed is:

1. An ultrasonic waveguide for guiding an ultrasonic signal situated in a predetermined frequency range, characterized in that the ultrasonic waveguide has a coiled foil (1) whose layer thickness is considerably less than the smallest wavelength of the ultrasonic signal in the predetermined frequency range in the foil material.

2. The ultrasonic waveguide according to claim 1, characterized in that the foil's (1) layer thickness is chosen thin enough that scattering and dispersion of the ultrasonic signal when it is being guided in the ultrasonic waveguide are largely suppressed.

3. The ultrasonic waveguide according to claim 1 or 2, characterized in that the frequency range is 15 kHz to 20 MHz.

4. The ultrasonic waveguide according to claim 3, characterized in that the foil's (1) layer thickness is less than 0.1 mm.

5. The ultrasonic waveguide according to claim 1 or 2, characterized in that the foil (1) is made of metal and/or ceramics and/or plastic.

6. The ultrasonic waveguide according to claim 1 or 2, characterized in that the foil (1) is inserted—preferably with a snug fit—into a—preferably metal—tube (2).

7. The ultrasonic waveguide according to claim 6, characterized in that the ends of the ultrasonic waveguide are welded—preferably TIG welded—and faced.

8. The ultrasonic waveguide according to claim 1 or 2, characterized in that the foil's (1) layer thickness changes from the inside toward the outside.

9. The ultrasonic waveguide according to claim 1 or 2, characterized in that the ultrasonic waveguide has several coiled foils (1) with different layer thicknesses and/or different materials.

10. The ultrasonic waveguide according to claim 1 or 2, characterized in that an ultrasonic transducer (4) is provided at one of the two ends of the coiled foil (1) in such a way that with it, ultrasonic signals can be input into the ultrasonic waveguide and/or can be received from the ultrasonic waveguide.

11. An ultrasonic flowmeter with an ultrasonic waveguide according to claim 1 or 2.

\* \* \* \* \*